United States Patent
Kusano

(10) Patent No.: US 8,469,708 B2
(45) Date of Patent: Jun. 25, 2013

(54) KIT FOR DIAGNOSING PULP EXPOSURE AND A PROBE SYRINGE

(76) Inventor: Kazunori Kusano, Tokyo (JP)

( * ) Notice: Subject to any disclaimer, the term of this patent is extended or adjusted under 35 U.S.C. 154(b) by 201 days.

(21) Appl. No.: 10/527,338

(22) PCT Filed: Sep. 16, 2004

(86) PCT No.: PCT/JP2004/013553
§ 371 (c)(1),
(2), (4) Date: Mar. 10, 2005

(87) PCT Pub. No.: WO2006/030511
PCT Pub. Date: Mar. 23, 2006

(65) Prior Publication Data
US 2006/0167372 A1    Jul. 27, 2006

(51) Int. Cl.
*A61C 3/00*    (2006.01)

(52) U.S. Cl.
USPC .......................................................... 433/32

(58) Field of Classification Search
USPC ... 433/32, 25, 80, 81, 224; 600/547; 604/187, 604/239, 240, 243; 222/566, 572; 156/293; 524/556, 13
See application file for complete search history.

(56) References Cited

U.S. PATENT DOCUMENTS

| | | | | |
|---|---|---|---|---|
| 2,986,542 | A * | 5/1961 | Schibler et al. | 524/598 |
| 3,916,529 | A * | 11/1975 | Mousseau | 600/547 |
| 4,105,715 | A * | 8/1978 | Gleave | 525/276 |
| 4,245,654 | A * | 1/1981 | Raitto | 600/578 |
| 4,944,678 | A * | 7/1990 | Villette | 433/224 |
| 5,964,737 | A * | 10/1999 | Caizza | 604/239 |
| 6,508,647 | B2 * | 1/2003 | Kusano | 433/81 |
| 6,607,631 | B1 * | 8/2003 | Badejo et al. | 156/327 |
| 6,889,433 | B1 * | 5/2005 | Enomoto et al. | 29/852 |
| 7,156,656 | B2 | 1/2007 | Duret | |
| 2002/0052580 | A1 * | 5/2002 | Ooyauchi | 604/240 |
| 2002/0168609 | A1 | 11/2002 | Kusano | |
| 2006/0088482 | A1 * | 4/2006 | Wulknitz et al. | 424/49 |
| 2006/0234189 | A1 | 10/2006 | Duret | |

FOREIGN PATENT DOCUMENTS

| | | |
|---|---|---|
| JP | 50-37296 | 4/1975 |
| JP | 60-103954 | 6/1985 |
| JP | 9-503932 | 4/1997 |
| JP | 2000-210309 | 8/2000 |
| JP | 2001-112782 | 4/2001 |
| JP | 2006-500133 | 1/2006 |
| WO | 95/04506 | 2/1995 |

(Continued)

OTHER PUBLICATIONS

Akio Tomita, "A Study of Examination Diagnosis of Pulpitis by an Electric Resistance Value", Journal of Oral Disease, vol. 29, pp. 304-319 (1962), accompanied by a partial English language Translation.

(Continued)

*Primary Examiner* — Sunil K Singh
(74) *Attorney, Agent, or Firm* — Westerman, Hattori, Daniels & Adrian, LLP

(57) ABSTRACT

Kit for diagnosing pulp exposure includes a probe syringe used for pulp exposure probe and a current detector device for obtaining a circuit resistance value or an impedance value from current flowing in an electric closed circuit including the probe syringe. The probe syringe further includes a discharge part formed with a flexible hollow material, a cylinder part continuous to the discharge part and retaining ion conductive paste, a piston inserted to the cylinder, and an electric conductive member connecting inside and outside of the probe syringe, and the current detector device obtains the circuit resistance value or impedance value flowing in the closed circuit through the ion conductive paste and displays the obtained value on a display part.

14 Claims, 8 Drawing Sheets

FOREIGN PATENT DOCUMENTS

WO 00/12050 3/2000
WO 2004/028626 4/2004

OTHER PUBLICATIONS

Yoshiko Hayashi, "A Clinical Observation for Pulp Diagnosis of Temporary Teeth and Prognosis Thereof by Electric Resistance Values", Journal of Child Dental Science, vol. 31, No. 2, pp. 290-295, (1982).

English Language Abstract of JP 2000-210309.
English Language Abstract of JP 60-103954, Jun. 8, 1985.
English Language Abstract of JP 2001-112782, Apr. 24, 2001.

* cited by examiner (a)

(b)

(c)

KIT FOR DIAGNOSING PULP EXPOSURE AND A PROBE SYRINGE

FIELD OF INVENTION

The present invention relates to a simple kit for diagnosing pulp exposure, and more particularly, relates to a kit for diagnosing exposed pulp through impedance measurement and a probe syringe used therefore.

Pulp exposure is defined as a condition in which a dental pulp becomes exposed in a oral cavity such that destruction of teeth reaches to the dental pulp tissue beyond hard tissues such as dentine. Normally, an exposed pulp is covered by destructed dentine, and hence, it is hard to observe visually such that the pulp exposure is diagnosed by a palpation test, a percussion test, a caloric test, an X-ray diagnosis, and an electric resistance test as well as a visual test.

Among above diagnosis tests, the palpation test, the percussion test and the caloric test may give extra stimulations to patients who complain of severe pain in most of cases and these tests are particularly not adequate to children. In order to avoid the above-described pain, it may be allowed to use anesthetic agents; however, usage of the anesthetic agents inevitably makes it impossible to conduct the palpation test or the percussion test and some patients can not accept any anesthetic agent because of his or hers allergy and other reasons. When the destructed dentine is removed from the tooth for the visual test, the anesthetic agent is often required, and then a kit for diagnosing pulp exposure with less stimulation to patients while avoiding usage of anesthetic agents. In the same reason, the method for diagnosing the pulp exposure by the X-ray photography may be avoided to particular patients such as gravida to whom X-ray exposure should be evaded if such exposure can be omitted from treatment.

In the above regards, several methods have been proposed in order to diagnose the pulp exposure using an electric property of dentine. For example, the method for electrically diagnosing the pulp exposure is conventionally known in which the pulp exposure is diagnosed by wetting a caries cavity with saline. In this method, first bottom of the caries cavity is wetted by saline to ensuring electronic conductivity, and thereafter, an electric resistance value between an electric conductive member contacted to cheek membrane at angulus oris and an electric conductive probe contacted to the bottom of the caries cavity. However, this method can not be applied to the case in which a exposed pulp part has a planer shape and then the part can not keep the saline. Therefore, when a cavity for keeping the saline is not present in the caries, the treatment beforehand such as formation treatment for keeping the saline is required. As the result, operations including dosing anesthetic agents to patients and then removing the destructed dentine are necessitated, and then merits of electric resistance measurement is not used sufficiently.

In a non-patent literature 1, a method for diagnosing the pulp exposure through an electric property is disclosed in which an electric contact property is improved with an electric conductive member having dental paste at the top of the member. Even in this method, it is necessary to touch the electric conductive member to the stimulation point. Therefore, the exposed pulp should be stimulated so that patients feel sudden and acute pain in many cases especially in cases of low age children. As describe above, in many cases, the aesthetic agent should be often applied beforehand when the pulp exposure is diagnosed using the electric property.

In addition, a non-patent literature 2 discloses the diagnosis of the pulp exposure using an electric resistance together with the visual test, a patent literature 3 discloses a method for diagnosing pulp exposure by supersonic waves and a probe therefor, and a patent literature 4 discloses a probe for touching live tissues in an oral cavity and equips a non-metal tip named as a super-probe. However, the methods disclosed in the above prior art literatures have been known, a kit for diagnosing pulp exposure, which makes it possible to simplify the diagnosis of the pulp exposure while reducing the pain to patients and may be placed inexpensively at a common dental clinic, is still expected.

Non-patent literature 1: Akio Tomita, "A study of examination diagnosis of pulpitis by an electric resistance value", Journal of Oral Disease, vol. 29, pp. 304-319, 1962.

Non-patent literature 2: Yoshiko Hayashi, "A clinical observation for pulp diagnosis of temporary teeth and prognosis thereof by electric resistance values", Journal of Child Dental Science, vol. 31, No. 2, pp. 290-295, 1982.

Patent literature 3: Japanese Patent (Laid-Open) Publication Heisei No. 9-503932.

Patent literature 4: Japanese Patent (Laid-Open) Publication No. 2000-210309.

Problem to be Solved by Invention

According to the above described conventional technique, an object of the present invention is to provide a kit for diagnosing pulp exposure and a probe syringe used therefor, in which pains to patients will be reduced effectively and the diagnosis of pulp exposure may be simplified and may be conducted in lower cost by electric resistance.

Means for Solving Problem

The inventor has found the fact that the pulp exposure can be detected by contacting ion conductive paste having predetermined viscosity to a caries cavity of a damaged tooth and has completed the present invention. That is, according to the present invention, a probe syringe containing the ion conductive paste is proposed. The probe syringe includes further an electric conductive part electrically connecting a tip of the syringe to outside of the syringe. The tip of the probe syringe is formed by a flexible and hollow discharge member. An end of the electric conductive member is disposed inside of the hollow discharge part. The other end of the electric conductive member is drawn out of the syringe through a predetermined portion of the syringe. The ion conductive paste is discharged to the caries cavity of the damaged tooth through an opening of the hollow discharge part.

The discharged ion conductive paste contacts to small unevenness of the caries cavity of the damaged tooth, and further deposition of the ion conductive paste allows to form a layer of the ion conductive paste. The above described operations may be conducted without contacting the caries cavity of the damaged tooth at all, and hence, any pain experienced by patients does not occur. The above treatments allows to form a circuit including inner portions of an oral cavity even when the ion conductive paste is being discharged without touching to the caries cavity. The current flowing through the exposed dental pulp in the caries cavity may be detected by a detection device using the electric resistance measurement or the impedance measurement through a terminal of the detection device connected to the angulus oris. When the caries causes pulp exposure, the display corresponding to the same resistance value with the resistance of the oral cavity to be about 6 k ohm is provided; however, when the caries does not causes pulp exposure, the display corresponding to higher resistance values to be about 15-20 k ohm.

The ion conductive paste has its viscosity which provides sufficient permeation ability to damaged dentine of the caries cavity and adequate adhesion to the damaged tooth so that the paste may provide certain electric conductivity while making it possible to form a conductive circuit without direct contact to the damaged portion. In addition, the ion conductive paste may be selected from various electric conductive compositions; however, when considering treatments after the diagnosis, the ion conductive paste is preferably selected from water-soluble paste and may include various water soluble salts or other electric conductive materials.

Thus according to the present invention, a kit for diagnosing pulp exposure is provided. The kit comprises a probe syringe used for a pulp exposure probe and a current detector device for obtaining a circuit resistance value or a circuit impedance value from current flowing an electric closed circuit including the probe syringe, The probe syringe further comprises a discharge part formed with a flexible hollow material, a cylinder part continuous to the discharge part and retaining ion conductive paste, a piston inserted to the cylinder part, and an electric conductive member connecting inner and outer areas of the probe syringe, The current detector device obtains the circuit resistance value or impedance value flowing the closed circuit through the ion conductive paste.

In the kit of the present invention, the discharge part is made from hollow silicone rubber, and the electric conductive member is disposed across the discharge part.

In the kit of the present invention, the ion conductive paste comprises an ion conductive material selected from the group consisted of propylene glycol, polyvinylalcohol, hydroxy-ethyl-cellulose, gelatin, polyacrylacid, carboxy-methyl-cellulose, sodium poly-acrylacid, sodium carboxy-methyl-cellulose.

According to the present invention, a probe syringe used for diagnosing pulp exposure is provided. The probe syringe comprising, a discharge part formed by a flexible hollow material, a cylinder part continuous to the discharge part and retaining ion conductive paste, a piston inserted to the cylinder, and an electric conductive member connecting inner and outer area of the probe syringe, wherein the electric conductive member allows to flow current through the ion conductive paste to form an electric conductive circuit including the ion conductive paste used as a prove for diagnosing pulp exposure.

In the present invention, the discharge part is made from hollow silicone rubber, and the electric conductive member is disposed across the discharge part.

In the present invention, the ion conductive paste comprises an ion conductive material selected from the group consisted of propylene glycol, polyvinylalcohol, hydroxy-ethyl-cellulose, gelatin, polyacrylacid, carboxy-methyl-cellulose, sodium poly-acrylacid, sodium carboxy-methyl-cellulose.

In the present invention, the ion conductive paste has the viscosity from 0.1 Pa·s to 5 Pa·s.

EXPLANATION OF NUMERALS

10-tooth, 12-articulation part, 14-dentine, 16-dental pulp, 18-caries part, 20-probe syringe, 22-ion conductive paste, 24-cylinder part, 26-piston, 28-discharge part, 30-electric conductive member

BEST MODE FOR PRACTICING INVENTION

Figure 1:
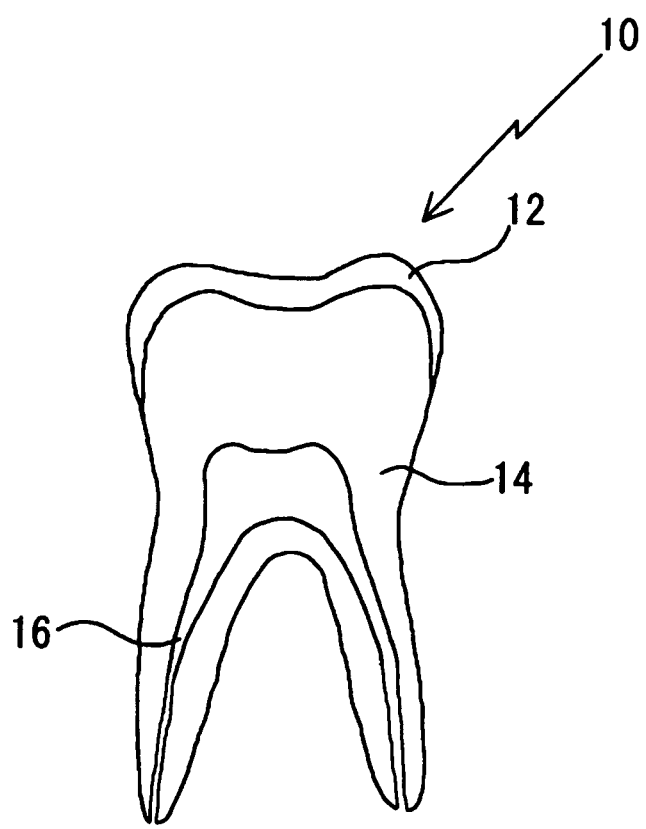
FIG. 1 shows a cross section of a tooth to which the present invention is applied.

FIG. 1 shows a schematic cross section of a tooth to which the present invention is applied. The tooth 10 comprises the articulation part 12, the dentine 14, and the dental pulp 16 covered with the dentine 14. Normally, it is known that a healthy tooth exhibits a high resistance value to be about 20 k ohm when an adequate water shield treatment is applied. On the other hand, when the dentine 14 of a health tooth is damaged by caries, electric conductive materials such as saliva penetrate to decalcification pars of the caries so that the tooth exhibits electric conductivity. Generally, the resistance of the oral cavity though the caries part is known to range from 10 k-13 k ohm to 20 k ohm. In addition, when the caries advances so as to reach to the dental pulp 16, the resistance shows fairly lower values. The dental pulp 16 extends to oral cavity tissues through inside of dentine such that the resistivity often becomes to 6.5 k ohm which corresponds approximately to a resistance value of the oral cavity. When the resistance value becomes such value, the dental pulp will be exposed when the caries part is removed under the treatment so that a direct pulp capping treatment, a pulp amputation treatment, or a pulpectomy treatment, which is never required in non-pulp exposure cases, may be required.

Figure 2:
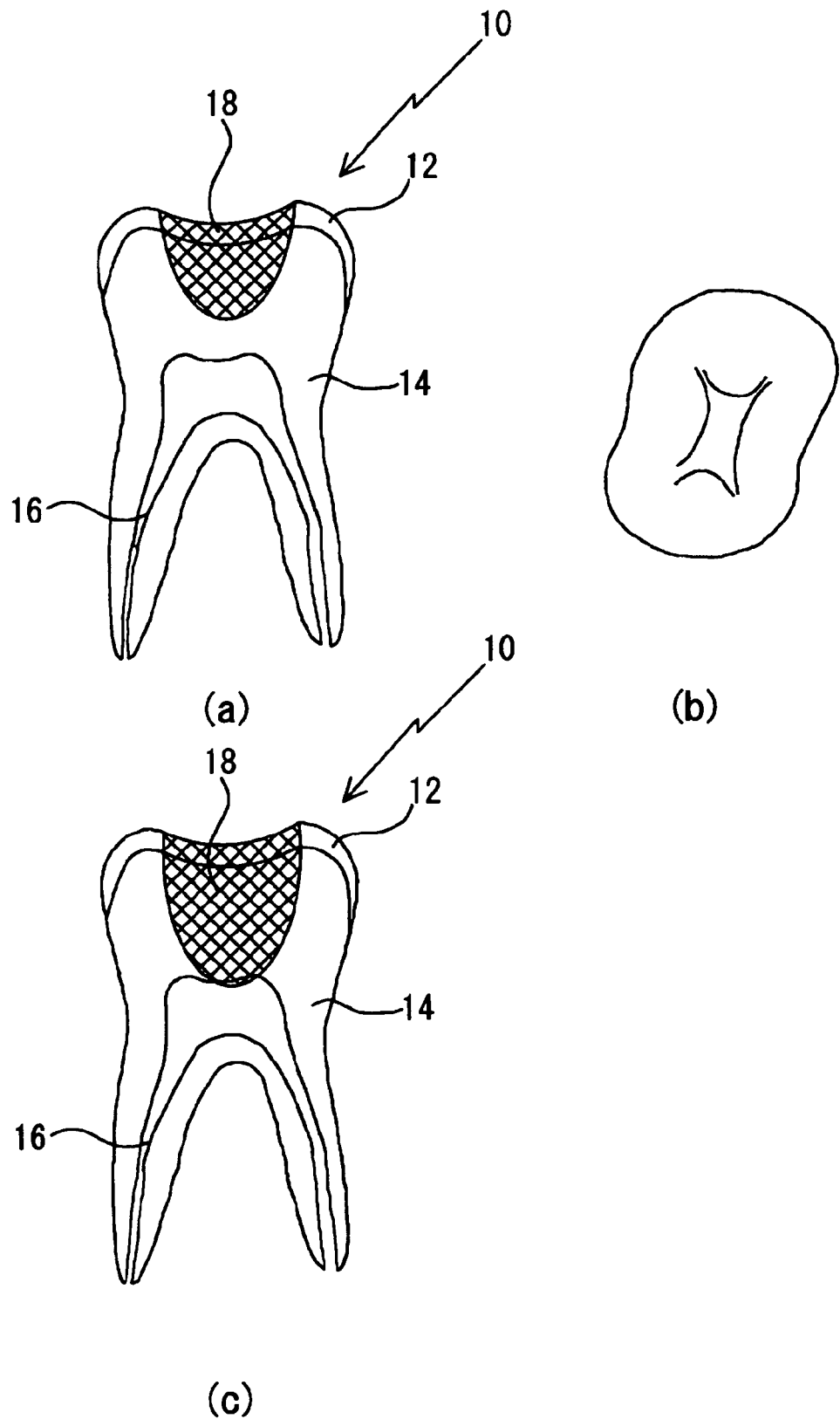
FIG. 2 shows a general cross section and plane views of the damaged tooth in which the destruction of the dentine is advanced.

FIG. 2 explains the advance of the caries resulting in the pulp exposure depicted in FIG. 1. In FIG. 2, the caries part is indicated by the areas with hatchings. Here, the caries part 18, depending on particular cases, sometimes forms a though hole from the surface of tooth to, for example, the dental pulp. As caries of the tooth 10 further advances, the caries part 18 is created as decalcified part of dentine (FIG. 2(a)), and when the caries part 18 further advances to reach to the dental pulp 16 (FIG. 2(c)), normally the dental pulp experiences external stimulation and finally pulpitis will be caused as the complication. In addition, when a patient comes to a dental clinic in order to receive treatments, the pulpitis has already become crisis as the complication. Even in such cases, pains and degrees of inflammation are different depending on each patient such that diagnosis of the pulp exposure can not be directly made even if strong pain and inflammation are observed. Furthermore, it is necessary to select treatment plans after the diagnosis from the possible treatments including the pulpectomy treatment or a tooth regeneration treatment depending on whether or not the caries advances to cause the pulp exposure in order to prepare the pulpectomy operation or the pulp amputation operation and to improve treatment efficiency by determining the treatment direction beforehand.

On the other hand, for the diagnosis of the pulp exposure, the caries part 18 must be removed, or the determination must be made through the caries part 18. When the caries part 18 is removed, it is necessary to apply the anesthetic treatment to suppress strong pains in most of the cases. When the pulp exposure is diagnosed by the electric resistance through the caries part 18, the conventional method requires physical contact with a metal probe to the caries cavity so that the anesthetic treatment beforehand is requested in order to remove pain or fears of patients. Another conventional method using the electric resistance assures the electric contact by saline; however, as shown in FIG. 2(b), the saline can not be kept on the damaged tooth, whereas a slight concave is formed on the surface of the tooth. Depending on the condition of the caries cavity, it is supposed that the saline can not kept in the cavity at all. In addition, the saline has no tixotropy property, and hence, a control of the flow after dropping the saline is difficult. Therefore, the present invention uses the probe syringe which contains the electric conductive paste with adequate viscosity in place of the saline and comprises a soft top part and an electric conductive member.

Figure 3:
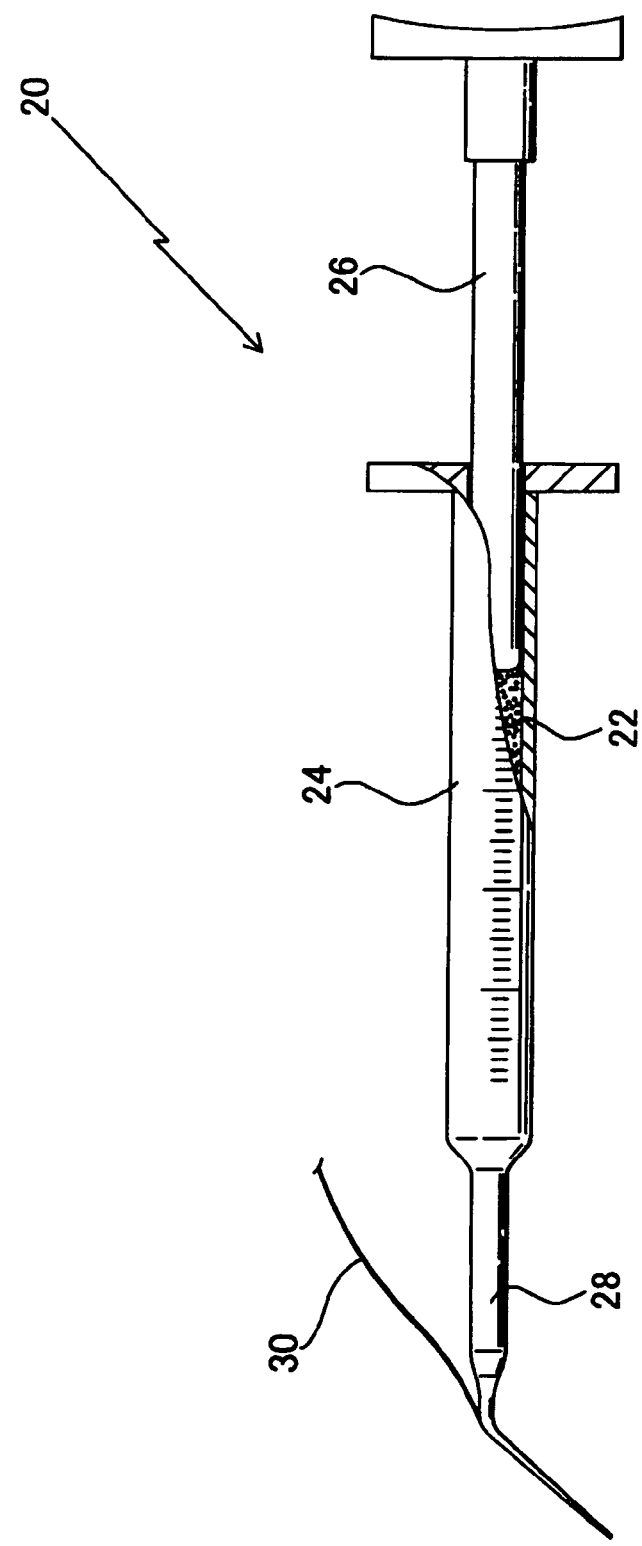
FIG. 3 shows a probe syringe of the present invention.

FIG. 3 shows an inside view of the probe syringe 20 according to the present invention. The probe syringe 20 comprises the cylinder part 24 which contains the ion conductive paste 22, the piston 26 inserted to the cylinder part 24 and the discharge part 28 disposed at the top of the cylinder part. The electric conductive member 30 such as a lead line is drawn outside the discharge part 28 such that electric conductivity is ensured between an inner part and an outer part of the syringe. The discharge part 28 may be formed by hollow silicone rubber and can form the electric conductive path through the ion conductive paste between the caries cavity and the electric conductive member under an non-contact condition. In addition, the discharge part may decrease stimulations to the dental pulp by flexibly bending even if the discharge part contacts to the caries part.

The ion conductive paste retained in the probe syringe may be selected from pastes having ion conductivity and aqueous dispersion. The ion conductive paste of the present invention may include such as, for example, dental paste or paste formed by dispersing or mixing carbon black, metal powder, metal oxide powder, various whisker, carbon nano-tube into other aqueous binders. Polymers used to prepare the ion conductive paste may include polypropylene glycol, polyvinylalcohol, hydroxy ethyl-cellulose, gelatine, polyacrylacid, carboxy-methyl-cellulose and sodium salts thereof, solbit and saline etc.

In addition, any known component may be included in the ion conductive paste of the present invention, and such components may be selected as a conventional dental paste compositions such as abrasives, viscosity agents, hardening agents, and surface active agents and may be further compounded sweeteners, preservation agents, effective ingredients, dyes, and flavors etc. The paste may be admixed the above ingredients and water to prepared thereof.

The abrasives may include silica-type abrasives such as silica-gel, precipitated silica, fumed silica, alumino-silicate, zircono-silicate, $CaHPO_4.2H_2O$, $CaHPO_4$ anhydride, $Ca_2P_2O_7$, aluminu hydroxide, alumina, titanium dioxide, crystal zirconium silicate, poly-methyl methacrylate, insoluble calcium meta-phospahe, precipitated calcium carbonate, heavy calcium carbonate, magnesium carbonate, magnesium tertiary phospate, zeolite, zirconium silicate, hydroxyapatite, fluoroapatite, calcium defect apatite, calcium tertiary phospahe, calcium quarter phospahe, calcium eighth phospahe, and synthesized polymer abrasives.

The viscosity agents my be selected from glycerin, solbit, propylene glycol, polyethylene glycol having its molecular weight between 200 and 6000, ethylene glycol, and polyalcohols such as reduced starch sugars etc. and these compounds may be selected one or two kinds or more.

In addition, the ion conductive paste of the present invention may include xanthane gum, sodium alginate, propylene glycol-alginate ester, carrageenan, carbopol (trade mark, acryl acid-alkyl acrylate copolymer), guar gum, gelatin, crystal cellulose as well as montmorillonite, kaolin, and bentonite.

Further to the ion conductive paste of the present invention, surface active agents may be added when such surface active agent is required. Such surface active agents may include anionic surface active agents, cationic surface active agents, nonionic surface active agents, and more particularly, may include sodium laurylsulfate, sodium N-lauroyl-taurine, N-acyl-sarcosinate, sodium alpha-olefine-sulfonate, N-acylglutamate, 2-alkyl-N-carboxymethyl-N-hydroxy-ethyl-imidasolinium betain, N-acyl-taurate, saccharide-fatty-acid-ester, alkylol amide, poly-oxyethylene solbitan mono-stearate, poloxanlene (pluronic), decaglycerin laurate etc.

For the purpose of treatments, sweetening agents or flavors may be added in order to reduce uneasiness of patients especially lower age such as children. The sweetening agents may include sodium saccharine, aspartame, stebioside, stebia essence, para-methoxy-cinnamaldehyde, neohesperidyl-hydro-chalkon, and perillartine etc. The preservation agents may be include such as paraben compounds such as butyl paraben, ethyl paraben, para oxy benzoic ester, sodium benzoate etc.

The flavors may include known flavor materials, for example, such as natural flavors peppermint oil, spearmint oil, anise oil, eucalyptus oil, wintergreen oil, acacia oil, clove oil, thyme oil, sage oil, lemon oil, orange oil, menthol oil, cardamon oil, coriander oil, mandarin oil, rime oil, lavender oil, rosemary oil, laurel oil, camomile oil, caraway oil, majoramu oil, bay oil, lemon glass oil, origanam oil, pine needle oil, neroli oil, rose oil, jasmine oil, iris pallida oil, absolute peppermint, absolute rose, orange flavor and flavors prepared by processing the natural flavors; and synthetic flavors such as, for example, menthol, carvone, anethole, cineole, methyl salicylate, cinnam aldehyde, eugenol, 3,1-menthoxy propane-1,2-diol, timor, linalol (*Thymus vulgaris* linalol), linalol acetate, limonene, menthone, menthol acetate, N-substituted-paramenthane-3-carboxamide, pinene, octyl aldehyde, citral, pulegone, carbinol acetate, anise aldehyde, ethyl acetate, ethyl buthylate, aryl-cycrohexan propionate, methyl anthranilate, ethylmetyl phenyl glycidate, vanillin, undeca lactone, hexanal, ethyl alcohol, propyl alcohol, buthyl alcohol, isoamyl alcohol, hexenol, dimethyl sulfide, cyclotene, furfural, trimethylpyrazine, ethyl lactate, ethyl tioacetate etc. as well as compounded flavors such as strawberry flavor, apple flavor, banana flavor, pineapple flavor, grape flavor, mango flavor, butter flavor, milk flavor, fruits-mix flavor, tropical fruits flavor etc.

Further to the above components, colorants may be included in the ion conductive paste of the present invention so as to improve a visual property. Such colorants used in the present invention may include brilliant blue FCF, CI 42090, yellow No. 4, CI 19140 or green No. 3, CI 42053 etc. A pH value of the ion conductive paste is not less than 6.5, more preferably, the pH may range from 7.0 to 10. Anesthetic agents such as lidocaine hydrochloride, propitocaine Hydrochloride, or citanest-octapressin may be added to the ion conductive agent of the present invention while making diagnosis of the pulp exposure and considering following operation.

The ion conductive paste preferably has the flow property which makes it possible to be kept to the caries cavity till the diagnosis will end. Furthermore, the ion conductive paste may be removed easily without brushing the paste from the cavity after completion of the pulp exposure diagnosis. From this stand point, the viscosity of the ion conductive paste may range from about dental paste to about glycerin at 25 Celsius degrees, more particularly may range from about 0.1 Pa·s to about 20 Pa·s which corresponds to the lowest viscosity of low viscosity dental paste. In addition, the ion conductive paste may preferably have the viscosity from about 0.1 Pa·s to about 5 Pa·s at 25 Celsius degrees the present invention in order to ensure excellent discharge properties and to provide adequate caries cavity adhesion. The viscosity of the ion conductive paste of the present invention may be measured by various methods and particularly the present invention may adopt the viscosity using a B-type viscometer at 25 Celsius degree.

Figure 4:
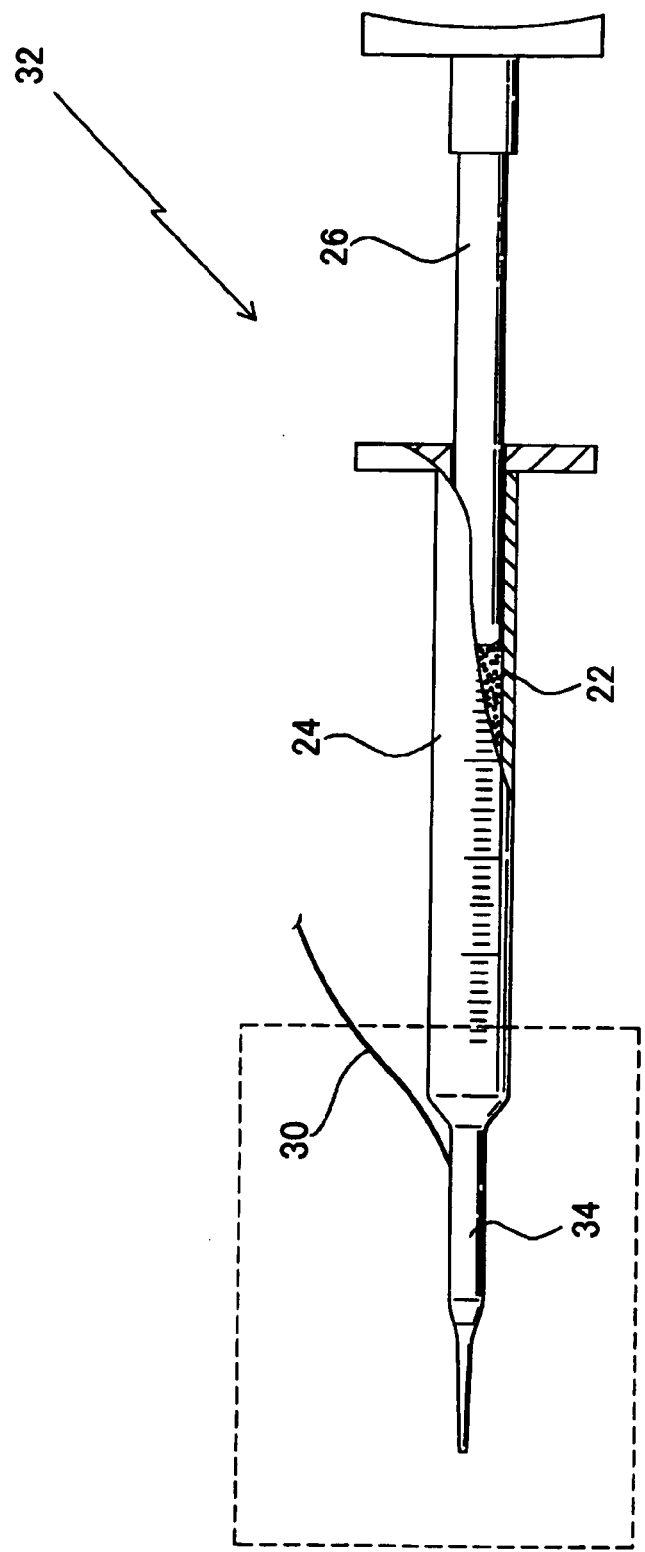
FIG. 4 shows a second embodiment of a probe syringe of the present invention.

FIG. 4 shows a second embodiment of the probe syringe of the present invention. The probe syringe 32 of FIG. 4 comprises almost a similar construction with the probe syringe shown in FIG. 3 except for the discharge part 34. The discharge part 34 of the probe syringe shown in FIG. 4 does not bend and therefore, the discharge property becomes improved. The discharge part 34 is formed by flexible silicone rubber as described in FIG. 3 so that the stimulation to the damaged portion may be decreased.

Figure 5:
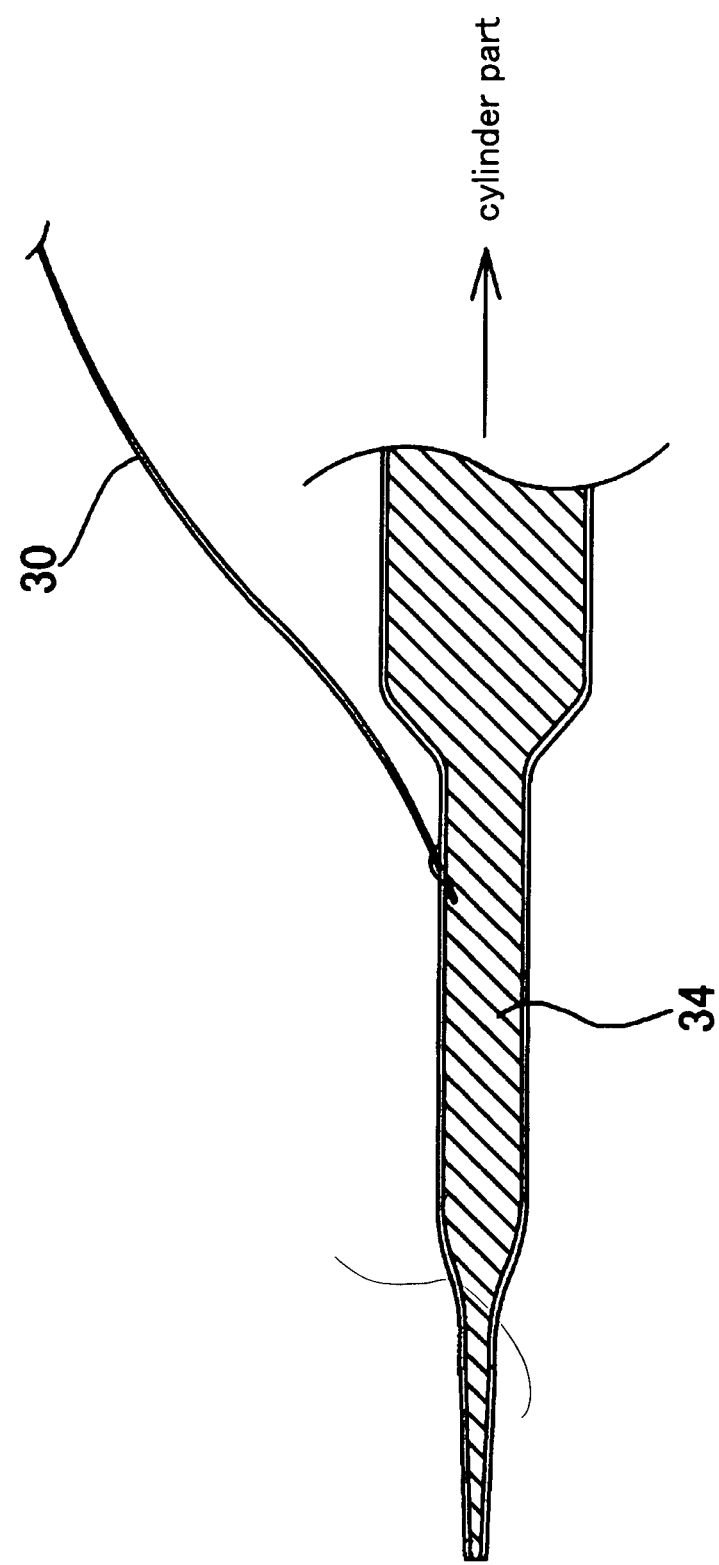
FIG. 5 shows a partial cross sectional view of a probe syringe according to the present invention.

FIG. 5 shows an enlarged cross section of the discharge part 34 of the probe syringe 32 in the second embodiment shown in FIG. 4 corresponding to the area indicated by dashed lines. As shown in FIG. 5, the inner area of the discharge part 34 is filled by the ion conductive paste and the electric conductive member 30 electrically connects the inner region and the outer region of the discharge part 34 by crossing the thickness of the discharge part 34. The electric conductive member 30 may be formed in a particular embodiment of the present invention by forming the discharge part 34, forming an opening, inserting the electric conductive member 30 into the opening and then sealing the opening together with an adequate adhesive such as a silicone type adhesive. Alternatively, in the another embodiment of the present invention, the electric conductive member 34 may be disposed such that the electric conductive member 30 extending through the discharge part 34 during or prior to a curing process in the production process of the discharge part 34 and then the silicone rubber may be cured to form the discharge part 34.

The electric conductive member 30 is introduced inside the discharge part 34 using the lead line as shown in FIG. 5. Alternatively, the electric conductive member 34 may be fixed securely to an inner wall of the discharge part 34 through an electronic conductive coating by soldering or spot welding the lead line to the coating. Furthermore, the electric conductive member 30 may be covered with an insulation coating from the position just exposed to the cylinder or may be fixed by some adhesive agents to the position adjacent to a dentist' hand along with the cylinder part 24 of the syringe. The electric conductive member 30 is extended into inside of the discharge part 34 so that the electric conductive path through the ion conductive paste may be shortened so as to improve a detection performance.

Figure 6:
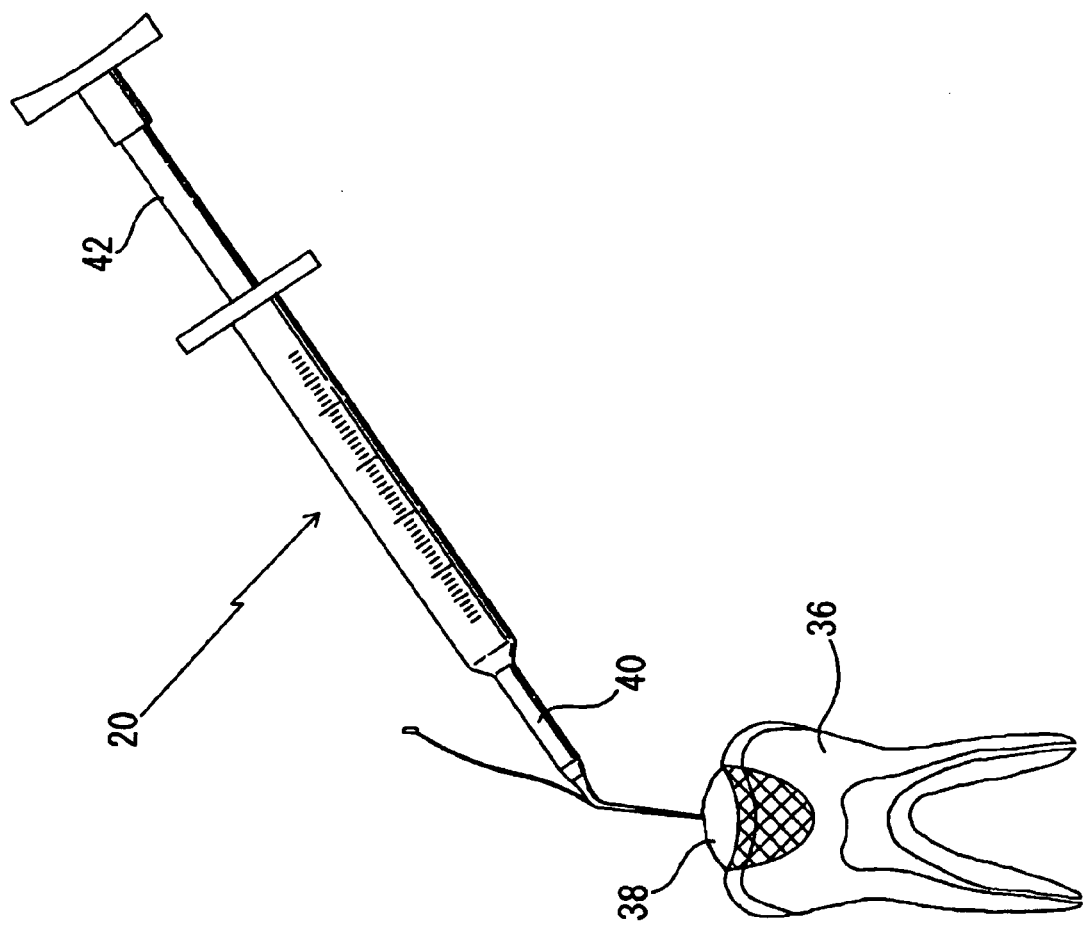
FIG. 6 shows a schematic view in which ion conductive paste is applied to a caries cavity according to the present invention.

FIG. 6 shows an embodiment of diagnosis of the pulp exposure using the probe syringe of the present invention. As shown in FIG. 6, the ion conductive paste discharged from the probe syringe 20 contacts to the damaged tooth 36 prior to the application of the anesthetic agent and forms the thick layer 38 of the ion conductive paste. The discharge part 40 of the probe syringe 20 is placed apart from the damaged tooth 36 from start of the discharge. The ion conductive paste is discharged to the caries cavity with controlled discharge amounts through the discharge part 40 by the pressure exerted to the piston part 42 so as to deposit the ion conductive paste layer 38.

Since the ion conductive paste contains a lot of ionic compounds, the ion conductive paste has similar electric conductivity with saline and also has adequate thixotropy due to the polymeric binder and various fillers such that the paste exhibits excellent deposition once it is discharged on the caries cavity even if only a shallow concave is present on the caries cavity. Therefore, the probe syringe of the present invention makes it possible to measure the electric resistance or impedance without contacting a hard material such as the probe directly to the damaged portion.

Figure 7:
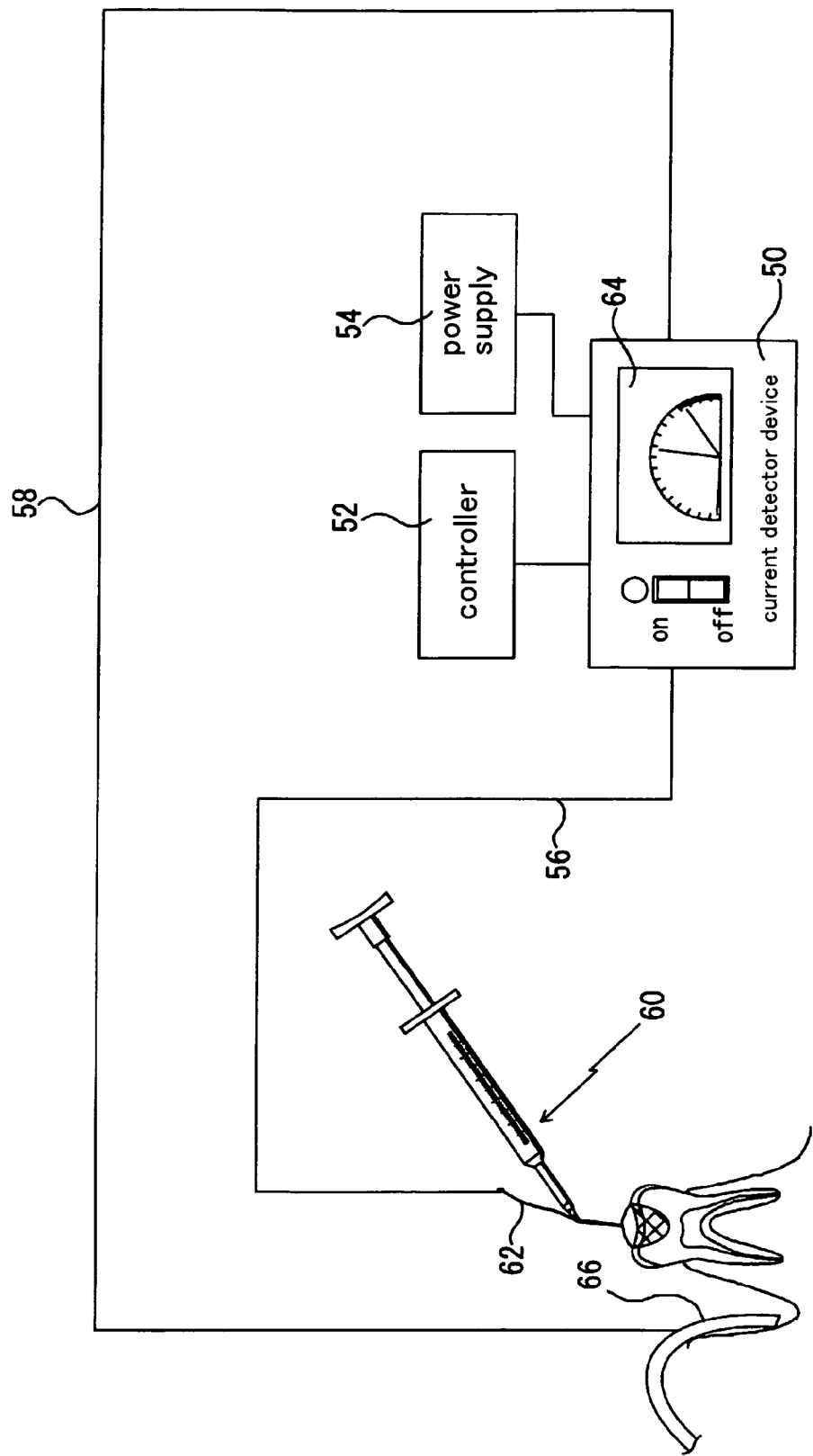
FIG. 7 shows a schematic view of a kit for diagnosing pulp exposure.

FIG. 7 shows the kit for diagnosing the pulp exposure using the probe syringe of the present invention. The kit for diagnosing the pulp exposure comprises a current detector device 50 which detects the current flowing from between the damaged tooth and the oral cavity so as to obtain the resistance while making it possible to detect the impedance when an alternative method is applied, a controller 52 for calculating the resistance or the impedance value by processing the current detected the current detector device while controlling the current detector device 50 so as not to provide over current, and a power supply 54 for providing the current to the closed circuit including the oral cavity. From the current detector device 50, the conduction lines 56, 58 are drawn and the one end of the conduction line 56 is equipped with the connector which is connected to the end of the electric conductive member 62 of the probe syringe 60. The end of the conduction line 58 may be attached to the suction tube 66 which is placed to the angulus oris.

Again referring to FIG. 7, the diagnosis of the exposed pulp is conducted by discharging the ion conductive paste from the probe syringe 60 and then forming the electric conductive path between the top of the probe syringe 60 and the caries cavity to flow the current. The current can be detected by the resistance value (impedance value) displayed on the display part 64 of the current detector device 50. The values indicated by the divisions may vary depending on the various particular performance of the current detector device; however, an healthy tooth has the resistance value at least about 20 k ohm and pseudo pulp exposure shows higher resistance (high impedance) to be 10-20 k ohm than that of true pulp exposure, and the true pulp exposure shows the resistance value (impedance value) to be 6.5 k ohm almost corresponding to the resistance of the oral cavity. Here, the pseudo pulp exposure is defined as the case in that the caries cavity does not reach to the dental pulp but the caries advances to the degree allowing the current to flow through thin dentine.

When the probe needle appearing to the display part 64 of FIG. 7 turns left at most, there is no possibility of the pulp exposure; when the probe needle appears about middle of the display, the pseudo pulp exposure can be suspected; and when the probe needle turns right at most, the resistance value or the impedance allowing dentists to diagnose as the true pulp exposure. Hereafter, the present invention will be explained with referring particular examples; however, the present invention can not be limited the examples described below.

EXAMPLES (Experimental 1)

Figure 8:
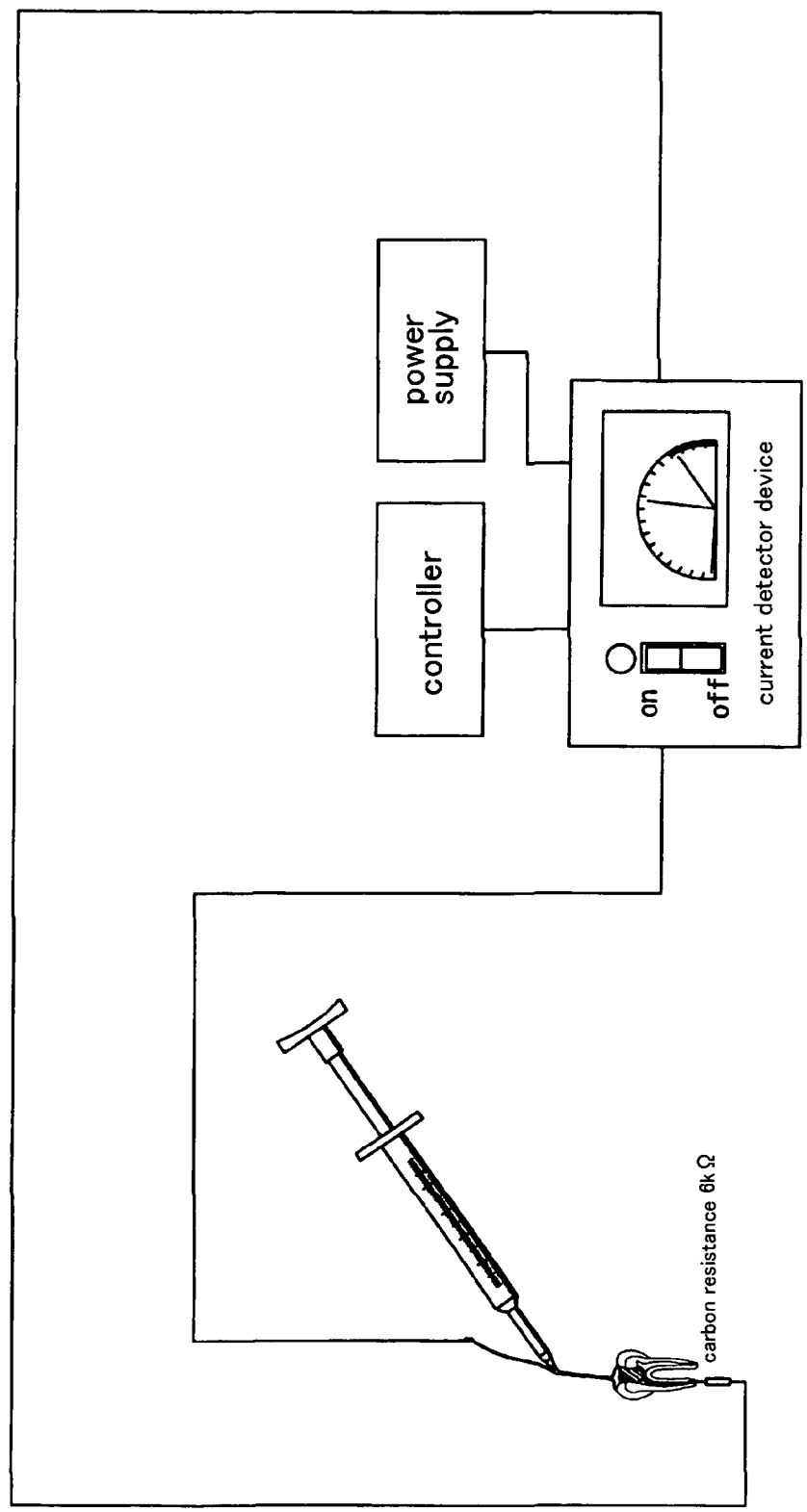
FIG. 8 shows a construction used for a simulation experiment of the present invention.

In FIG. 8, the practical construction of the kit for diagnosing the pulp exposure used in the simulation experiment of the present invention is depicted. In the probe syringe of FIG. 8, dental paste commercially available (including carboxy methyl cellulose is included therein) was used as the ion conductive paste after diluting the dental paste by saline to be the viscosity range from 0.1-0.2 Pa·s so that the ion conductive paste had fluidity enough to be discharged through the probe syringe. The ion conductive paste was filled in an empty probe syringe to prepare the probe syringe.

A commercially available root canal meter for EMR measurement was used as the current detector device which was a device used to measure root canal length detector. A model caries tooth was prepared using an extracted caries tooth without pulp and a lead line of a carbon resistance of 6 k ohm was introduced into an adequate position of a root canal from the lower side of a root canal apex and then covered by absorbent cotton wetted with saline. Another end of the carbon resistance was connected to a clip of the root canal meter. In addition, the electric conductive member of the probe syringe was connected with the other conductive line of the root canal meter. In this condition, the ion conductive paste was discharged above the damaged tooth. The ion conductive paste was retained excellently thereon. The probe needle of the root canal meter was swung to the region corresponding to the pulp exposure as high as the resistance value of the oral cavity.

(Experimental 2)

A similar experiment was conducted using the kit for diagnosing the pulp exposure as the experimental 1 and dry absolute cotton without wetting the saline. At the start of the experiment, the probe needle was swung to the position corresponding to the high impedance; however, saline included in the ion conductive paste penetrated to the absolute cotton and became to contact to the lead line of the carbon resistance, it was confirmed that the probe needle swung gradually to the position corresponding to the low impedance. That is, impedance values in response to degrees of caries cavity from the surface of damaged tooth to the dental pulp.

Industrial Availability

As described above, according to the present invention, the diagnosis of the pulp exposure may be conducted easily and at low cost. In addition, according to the present invention, the diagnosis of the pulp exposure may be conducted without applying anesthetic agents beforehand while not providing excess loads to patients. Furthermore, according to the present invention, the ion conductive paste may be removed easily by gargling after the diagnosis, and hence the pulp exposure may be operated without degrading operability of removal of the caries portion.

The invention claimed is:

1. A kit, said kit comprising:
a probe syringe, and
a current detector device which obtains a circuit resistance value or a circuit impedance value from current flowing in an electric closed circuit including said probe syringe,
wherein said probe syringe comprises
a thixotropic aqueous dispersed ion conductive paste adapted to be deposited as a layer of ion conductive paste on a tooth,
a discharge part formed from a flexible hollow material and being positioned on a top of said probe syringe, the discharge part forming an electrical conductive path of the thixotropic ion conductive paste between the tooth and an electrical conductive member,
a cylinder part continuous with said discharge part and retaining said thixotropic aqueous dispersed ion conductive paste,
a piston inserted to said cylinder part, and
an electric conductive member which ensures electrical conductivity between an inner part and an outer part of the syringe connecting inner and outer areas of said probe syringe, and
wherein said current detector device obtains said circuit resistance value or impedance value flowing in said closed circuit through said thixotropic ion conductive paste.

2. The kit of claim 1, wherein said discharge part is made from hollow silicone rubber, and said electric conductive member is disposed across said discharge part.

3. The kit of claim 1, wherein said thixotropic ion conductive paste comprises a thixotropic ion conductive material selected from polyvinylalcohol, hydroxy-ethyl-cellulose, gelatin, polyacrylacid, carboxymethyl-cellulose, sodium poly-acrylacid, and sodium carboxy-methyl-cellulose.

4. A probe syringe, said probe syringe comprising:
a thixotropic aqueous dispersed ion conductive paste adapted to be deposited on a tooth,
an electric conductive member connecting an inner area and an outer area of said probe syringe, thereby ensuring electric conductivity between said inner part and said outer part of said probe syringe,
a discharge part formed from a flexible hollow material and being positioned on a top of said probe syringe, the discharge part forming an electrical conductive path of the thixotropic ion conductive paste between the tooth and the electrical conductive member,
a cylinder part continuous with said discharge part and retaining the thixotropic aqueous dispersed ion conductive paste, and
a piston inserted to said cylinder part,
wherein said electric conductive member allows current to flow through said thixotropic ion conductive paste to form an electric conductive circuit including said ion conductive paste.

5. The probe syringe of claim 4, wherein said discharge part is made from hollow silicone rubber, and said electric conductive member is disposed across said discharge part.

6. The probe syringe of claim 4, wherein said thixotropic ion conductive paste comprises an ion conductive material selected from polyvinylalcohol, hydroxy-ethyl-cellulose, gelatin, polyacrylacid, carboxymethyl-cellulose, sodium poly-acrylacid, and sodium carboxy-methyl-cellulose.

7. The probe syringe of claim 6, wherein said ion conductive paste has the viscosity from 0.1 Pa·s to 5 Pa·s.

8. A kit, said kit comprising:
a probe syringe, and
a current detector device which obtains a circuit resistance value or a circuit impedance value from current flowing in an electric closed circuit including said probe syringe,
wherein said probe syringe comprises
a thixotropic aqueous dispersed ion conductive paste adapted to be deposited as a layer of ion conductive paste on a tooth,
a discharge part formed from a hollow material and being positioned on a top of said probe syringe, the discharge part forming an electrical conductive path of the thixotropic ion conductive paste between the tooth and an electrical conductive member,
a cylinder part continuous with said discharge part and retaining said thixotropic aqueous dispersed ion conductive paste,
a piston inserted to said cylinder part, and
an electric conductive member which ensures electrical conductivity between an inner part and an outer part of the syringe connecting inner and outer areas of said probe syringe, and wherein said current detector device obtains said circuit resistance value or impedance value flowing in said closed circuit through said thixotropic ion conductive paste.

9. The kit of claim 8, wherein said discharge part is made from hollow silicone rubber, and said electric conductive member is disposed across said discharge part.

10. The kit of claim 8, wherein said thixotropic ion conductive paste comprises a thixotropic ion conductive material selected from polyvinylalcohol, hydroxy-ethyl-cellulose, gelatin, polyacrylacid, carboxymethyl-cellulose, sodium poly-acrylacid, and sodium carboxy- methyl-cellulose.

11. A probe syringe, said probe syringe comprising:
a thixotropic aqueous dispersed ion conductive paste adapted to be deposited on a tooth,
an electric conductive member connecting an inner area and an outer area of said probe syringe, thereby ensuring electric conductivity between said inner part and said outer part of said probe syringe,
a discharge part formed from a hollow material and being positioned on a top of said probe syringe, the discharge part forming an electrical conductive path of the thixotropic ion conductive paste between the tooth and the electrical conductive member,
a cylinder part continuous with said discharge part and retaining the thixotropic aqueous dispersed ion conductive paste, and
a piston inserted to said cylinder part,
wherein said electric conductive member allows current to flow through said thixotropic ion conductive paste to form an electric conductive circuit including said ion conductive paste.

12. The probe syringe of claim 11, wherein said discharge part is made from hollow silicone rubber, and said electric conductive member is disposed across said discharge part.

13. The probe syringe of claim 11, wherein said thixotropic ion conductive paste comprises an ion conductive material selected from polyvinylalcohol, hydroxy-ethyl-cellulose, gelatin, polyacrylacid, carboxymethyl-cellulose, sodium poly-acrylacid, and sodium carboxy- methyl-cellulose.

14. The probe syringe of claim 13, wherein said ion conductive paste has the viscosity from 0.1 Pa·s to 5 Pa·s.

* * * * *